United States Patent
Karvonen

(10) Patent No.: US 10,752,851 B2
(45) Date of Patent: Aug. 25, 2020

(54) ARRANGEMENT AND METHOD FOR PREPARING A GAS

(71) Applicant: ForestGas Oy, Uusikylä (FI)

(72) Inventor: Teuvo Karvonen, Lahti (FI)

(73) Assignee: ForestGas Oy, Uusikylä (FI)

( * ) Notice: Subject to any disclaimer, the term of this patent is extended or adjusted under 35 U.S.C. 154(b) by 22 days.

(21) Appl. No.: 16/066,505

(22) PCT Filed: Dec. 30, 2016

(86) PCT No.: PCT/FI2016/050939
§ 371 (c)(1),
(2) Date: Jun. 27, 2018

(87) PCT Pub. No.: WO2017/115019
PCT Pub. Date: Jul. 6, 2017

(65) Prior Publication Data
US 2019/0002777 A1    Jan. 3, 2019

(30) Foreign Application Priority Data
Dec. 30, 2015  (FI) ................................ 20156029

(51) Int. Cl.
*C10J 3/78* (2006.01)
*C10L 3/08* (2006.01)
(Continued)

(52) U.S. Cl.
CPC ............... *C10J 3/78* (2013.01); *C01B 3/02* (2013.01); *C07C 1/041* (2013.01); *C07C 1/0485* (2013.01);
(Continued)

(58) Field of Classification Search
CPC ..................................... C01B 3/02; C10J 3/78
See application file for complete search history.

(56) References Cited

U.S. PATENT DOCUMENTS

| 2010/0197879 A1* | 8/2010 | De Broqueville | ....... B01J 8/386 526/348 |
| 2010/0258429 A1* | 10/2010 | Ugolin | .................... C10L 9/083 204/157.43 |

(Continued)

FOREIGN PATENT DOCUMENTS

| CN | 103030206 B | 5/2014 |
| DE | 4417082 C1 | 10/1995 |

(Continued)

OTHER PUBLICATIONS

European Patent Office, Supplemental Search Report of European patent application EP16881331, dated Jul. 12, 2019, 3 pages.

(Continued)

*Primary Examiner* — Matthew J Merkling
(74) *Attorney, Agent, or Firm* — Berggren LLP

(57) ABSTRACT

The invention relates to an arrangement for preparing a gas in a closable reactor by supplying the reactor with carbon-based biomass or chopped wood material, such as chips, in substantially oxygen-free conditions, by allowing the biomass or wood material to gasify at a high temperature, and by recovering the gas generated in a gasification reaction. In that the arrangement the reactor has its interior defined by a feed pipe whose inlet end is closable with a shut-off valve, especially with a ball valve, and whose outlet end adjoins a heatable gasification dome, biomass or chopped wood material is delivered from the feed pipe's inlet end into the reactor's interior, the reactor's interior is supplied with free water/water vapor in its supercritical state, which is optionally prepared catalytically by splitting water/water vapor, the biomass or wood material is conveyed into a gasification space of the reactor's interior, which is in connection with the heated gasification dome and which is adapted to have existing conditions selected in a manner such that the water (Continued)

present in said gasification space is present in its supercritical state, and the gas generated in the gasification reaction is recovered.

24 Claims, 3 Drawing Sheets

(51) Int. Cl.
*C10J 3/30* (2006.01)
*C10J 3/10* (2006.01)
*C01B 3/02* (2006.01)
*C07C 1/04* (2006.01)

(52) U.S. Cl.
CPC ............... *C10J 3/10* (2013.01); *C10J 3/30* (2013.01); *C10L 3/08* (2013.01); *C07C 2523/755* (2013.01); *C10J 2200/09* (2013.01); *C10J 2200/154* (2013.01); *C10J 2300/092* (2013.01); *C10J 2300/0946* (2013.01); *C10J 2300/0973* (2013.01); *C10J 2300/0979* (2013.01); *C10J 2300/1276* (2013.01); *C10J 2300/1621* (2013.01); *C10J 2300/1662* (2013.01); *Y02P 20/544* (2015.11)

(56) References Cited

U.S. PATENT DOCUMENTS

| | | | |
|---|---|---|---|
| 2011/0209698 A1* | 9/2011 | Mulcahy | C10J 3/26 126/85 R |
| 2011/0308511 A1* | 12/2011 | Player | F23B 40/04 126/152 R |
| 2012/0029095 A1* | 2/2012 | Junaedi | B01J 19/2495 518/706 |
| 2012/0060418 A1 | 3/2012 | Epstein et al. | |
| 2012/0277327 A1* | 11/2012 | Han | B01J 8/067 518/702 |
| 2015/0014183 A1* | 1/2015 | Akay | B01J 37/0221 205/462 |

FOREIGN PATENT DOCUMENTS

| | | |
|---|---|---|
| DE | 10259928 A1 | 7/2004 |
| JP | H06299169 A | 10/1994 |
| JP | 3469604 B2 | 11/2003 |
| WO | 9630464 A1 | 10/1996 |
| WO | 2013030028 A1 | 3/2013 |
| WO | 2014149045 A1 | 9/2014 |

OTHER PUBLICATIONS

Finnish Patent Office, search report issued in FI patent application No. 20156029 dated Jul. 8, 2018.

* cited by examiner

ARRANGEMENT AND METHOD FOR PREPARING A GAS

PRIORITY

This application is a U.S national application of the international application number PCT/FI2016/050939 filed on Dec. 30, 2016 and claiming priority of Finnish national application FI 20156029 filed on Dec. 30, 2015, the contents of all of which are incorporated herein by reference.

FIELD OF INVENTION

The invention relates to an arrangement for preparing a gas in a closable reactor by supplying said reactor with biomass or chopped wood material, especially chips, in substantially oxygen-free conditions, by allowing the biomass or chopped wood material to gasify at a high temperature, and by recovering a (gasification) gas generated in the gasification reaction.

The invention relates also to an arrangement for preparing a gas in a closable reactor by supplying said reactor with plastic material or plastic-based material in substantially oxygen-free conditions, by allowing the plastic material or plastic-based material to gasify at a high temperature, and by recovering a gas generated in gasification reaction.

BACKGROUND

In the production of wood gas particularly from wood material, and even more specifically from chips, several options are available.

From wood material, such as chips, can be produced wood gas by introducing excess air into a fuel and air mixing chamber or mixer head. In this case, however, the resulting gas contains a fairly large amount of unburned inert nitrogen gases and the combustion value of generated wood gas per unit of supplied wood material remains low.

In case an attempt is made to increase the amount of gas per unit of supplied wood material by introducing pure oxygen into the mixer head, the production costs will rise dramatically because of the price of oxygen feed.

Both foregoing problems are at least partially avertable in so-called pyrolysis, wherein wood material, such as chips, is heated while attempting at the same time to avoid the passage of air or oxygen into the mixer head or gasification space. Although the pyrolysis of wood material, such as chips, provides a solution to the foregoing problems relating to the produced gas having a low combustion value per unit of supplied wood material, one major problem in pyrolysis results from impurities which migrate from wood material to gas fraction and hamper further processing of the product for example with a well-known Fischer-Tropsch process, and from impurities, most notably tars, which are left in so-called pyrolysis oil as a result of incomplete combustion. The elimination of impurities contained in pyrolysis oil and in gas fraction entails normally a considerable increase in pyrolysis costs.

The pyrolysis-generated impurities can be reduced with a so-called ablative pyrolysis in which wood material, such as chips, is gasified at a high temperature and at a relatively high pressure, but the problem here turns out to be a low conversion of wood material, resulting in 30-35% of unburned carbon residue per kilogram of supplied dry wood material.

SUMMARY OF THE INVENTION

Accordingly, it was an objective of the invention to obviate the drawbacks present in the foregoing prior art by providing an arrangement, as well as a method, for the gasification of wood material, especially chips, in such a manner that the gasification would be based on enhanced pyrolytic decomposition of wood material such as chips by heating the chips in oxygen-free conditions to enable a removal of pyrolysis oils as well as tars normally present in pyrolysis and of impurities present in chips gasification gases. At the same time, however, it was an objective to provide as high a conversion as possible of wood material into gasification gases in such a way that the amount of non-gasified carbon residue in ash would be as small as possible.

It was another objective of the invention to provide a method and an arrangement which would enable a control and management of the gasification process to be conducted in a precise and versatile manner. A further objective of the invention was to provide an arrangement that would also enable the gasification of plastics or a plastic-based material. At the same time, however, it was an objective to provide the gasification gas with a combustion value or energy content as high as possible calculated per kilogram of supplied dry wood material.

It was another objective of the invention to provide energy efficient reaction conditions.

The foregoing objectives are attained with an arrangement and a method for preparing a gas as disclosed and claimed herein.

More specifically, the invention relates to an arrangement for preparing a gas in a closable reactor by supplying said reactor with carbon-based biomass or chopped wood material, especially chips, in substantially oxygen-free conditions, by allowing the chips to gasify at a high temperature, and by recovering the gas (G) generated in a gasification reaction. In the arrangement a reactor's interior is defined by a feed pipe whose inlet is closable with a shut-off valve, especially with a ball valve, and whose outlet end adjoins a heatable gasification dome, comminuted biomass or chopped wood material is delivered from a bottom end of the feed pipe into the reactor's interior, the reactor's interior is supplied with free water/water vapor (V), preferably in its supercritical state, which is optionally prepared catalytically by splitting the water/water vapor (V), the biomass or wood material is conveyed into the reactor interior's gasification space, which is in connection with the heated gasification dome and which is adapted to have existing conditions selected in a manner such that the water (V) present in said gasification space is present in its supercritical state, the gas (G) generated in the gasification reaction is recovered.

In one embodiment of the invention, the reactor is elongated.

The invention relates also to an arrangement in which the biomass or wood-based material is here replaced by using a plastic material or a plastic-based material.

The invention relates also to a method for preparing a gas in a closable reactor by supplying said reactor with carbon-based biomass or chopped wood material, especially chips (H), in substantially oxygen-free conditions, by allowing the biomass or wood material to gasify at a high temperature and by recovering a resulting gas (G). The method comprises:

conveying the biomass or wood material into the reactor's gasification space, which is adapted to have existing conditions selected in a manner such that water (V) present in said gasification space is present in its supercritical state, supplying the reactor's interior, preferably the gasification space, with free water/steam (V) preferably in its supercritical state.

The supercritical water refers to a state of water in which the separate vapor and liquid phases of water are no longer distinguishable but, instead, water is present in the form of a supercritical fluid in which the liquid and gaseous forms of water are in equilibrium. Water is present in the form of a supercritical fluid when it is above a certain supercritical point at which it has a pressure of 22.064 Mpa (about 217 bar) and a temperature of 647 K (374° C.)

The carbon-based biomass refers in this disclosure to so-called energy waste or combustible wood, logging waste, as well as plants with a content of sugar and starch.

In a preferred embodiment of the invention, the gasification space is adapted to have an existing pressure of not less than 220 bar and a temperature of 374° C.

The principal components of a gasification gas G generated in a chips gasification reaction of the invention are $H_2$, CO, $CO_2$, $CH_4$ and possibly some higher hydrocarbons, depending on a temperature of the gasification space. However, by a higher partial pressure of water in a gasification reaction (R)

$$CO + H_2O \leftrightarrow CO_2 + H_2 \quad (2)$$

the reaction is controlled in such a way that a majority of the gasification gas (G) consists of hydrogen gas, nor is there present hardly any higher hydrocarbons.

A significant benefit attained with a method and arrangement of the invention is a capability of controlling the gasification process effectively so as to efficiently minimize the amount of impurities in a gasification gas or in a product gas obtained from methanation of the gasification gas.

Supplementing the reactor's interior, preferably the gasification chamber, with free water/steam N), preferably in its supercritical state, provides an ability to improve the process considerably in terms of its manageability and control as compared to the situation in which the water/steam would all be delivered along with a material, such as biomass or chips, to be supplied into the process.

Along with added supercritical water/water vapor, the process can, among others, be supplied with precisely measured additives e.g. for reducing the amount of tar and for optimizing energy production on the basis of the composition, water content of the material to be supplied into the process.

In one preferred embodiment of the invention, biomass or chopped wood material is supplied from an inlet end of the feed pipe into the reactor's interior. The water content held by supplied biomass or chopped wood material and/or the amount and type of impurities contained in biomass or chopped wood material will be measured or assessed.

The measured or assessed water content of supplied biomass or chopped wood material is used as a basis for regulating the amount of free water/steam supplied into the reactor's interior, preferably into the gasification space. The water content of biomass or chopped wood material can be assessed or measured before or after its delivery into the reactor's interior.

By measuring the supplied biomass/chips for its water content and by then using the measurements as a basis for dispensing free supplementary water/supplementary steam into the gasification dome or inside the reactor, it is after the delivery that an effective feedback adjustment can be accomplished. The process control provides a capability of controlling the process in a manner that is faster, more precise, and more versatile than in methods known from the prior art: publications WO2013030028, WO9630464 and JPH06299169, among others, have proposed methods for the gasification of chips and biomass, wherein the entire amount of water/steam to be introduced into the process arrives along with the chips/biomass supply. Such a process is considerably more inconvenient to regulate than the one provided by the invention, because, for example, the feedback control is awkward and less precise. This is caused by fluctuations in the amount of water contained in the material, by the slowness of effects to be attained by changes made in the supply flow, etc.

In one preferred embodiment of the invention, along with the free supercritical there are also supplied additives which enable the binding of materials possibly contained in the feed and detrimental to further process, or materials whose bonding to ash is desirable.

Such additives include for example various calcium compounds, which may enable alkali metals to be bonded to ash, such as potassium, contained in wood, thereby improving the fertilizer value of ash. In addition, the use of calcium compounds provides a capability of binding as calcium sulfate for example the sulfur S present in wood, which may otherwise cause problems as the process continues. Furthermore, along with supercritical water added into the reactor, it is possible to introduce also other additives which can be used for scrubbing the gasification gas or for changing the composition of a gasification gas to be produced; several waste materials, such as various types of plastic, contain a considerable amount of various additives which might cause problems in the use of a gasification gas when incorporated in the process feed. The introduction of purifying additives directly into a material to be supplied into the reactor is considerably more awkward and inaccurate than the introduction of said additives directly into the gasification dome in connection with the supply of supercritical water/steam.

A major benefit attained by the use of high pressure is that the amount of produced tars is very small, i.e. the produced gasification gas G is very pure in and of itself.

The gas can be purified further by converting impurities left in the gas into a form soluble in water or in an aqueous solvent. For example, along with supercritical water it is possible to create in the reactor reaction conditions which enable impurities to be reduced or the form of impurities to be converted in the outgoing gas. Hence, in one preferred embodiment of the invention, the reactor is supplied, along with supercritical water, with an oxygen-binding substance such as carbon or sodium.

In yet another preferred embodiment of the invention, between the reactor's gasification dome and feed pipe is located a gasification dome's discharge opening by which the gasification gas G generated in the gasification space and the ash are able to exit into the reaction chamber's discharge space in such a way that the gasification gas G passes through the ash. Thereby, it is possible to have solid impurities of the gas bonded with ash.

Still further, the method and arrangement of the invention enable a minimization of the amount of carbon in the ash discharging from the gasification space.

In the arrangement and method of the invention, water is present in the gasification space in its supercritical state. This provides a considerable benefit in the sense that the complete gasification of wood is accomplished at a temperature as low as about 374° C., preferably at a temperature higher than 700° C., thereby enabling a minimization of the carbon content of ash.

Likewise, the high pressure (217 bar, preferably more than 220 bar), used in the arrangement and method of the invention, reduces the carbon content of ash produced in the gasification reaction (R).

Indeed, using the method and arrangement of the invention enables an achievement of very low carbon contents in ash discharging from the gas space—the carbon content is extremely low, less than 1%, preferably less than 0.5%—as a result of a high pressure used in the gasification reaction and the presence of supercritical water in the reaction.

In one preferred embodiment of the invention, the reactor's interior has its gasification space 30; 31 supplied with water V; V2 in supercritical state for increasing the amount of carbon dioxide and hydrogen in what takes place in the gasification space 30, 31 as a gasification reaction R:

$$CO+H_2O \leftrightarrow +CO_2+H_2 \quad (2)$$

Thus, the gasification gas G (or subsequently also simply the gas), generated in the reaction R, has a ratio $H_2/CO>2$. Thereby is provided the significant benefit that the gas can be synthesized for example with Fischer-Tropsch synthesis.

SHORT DESCRIPTION OF THE FIGURES

The invention will now be described with reference to the accompanying figures.

DETAILED DESCRIPTION

Figure 1:
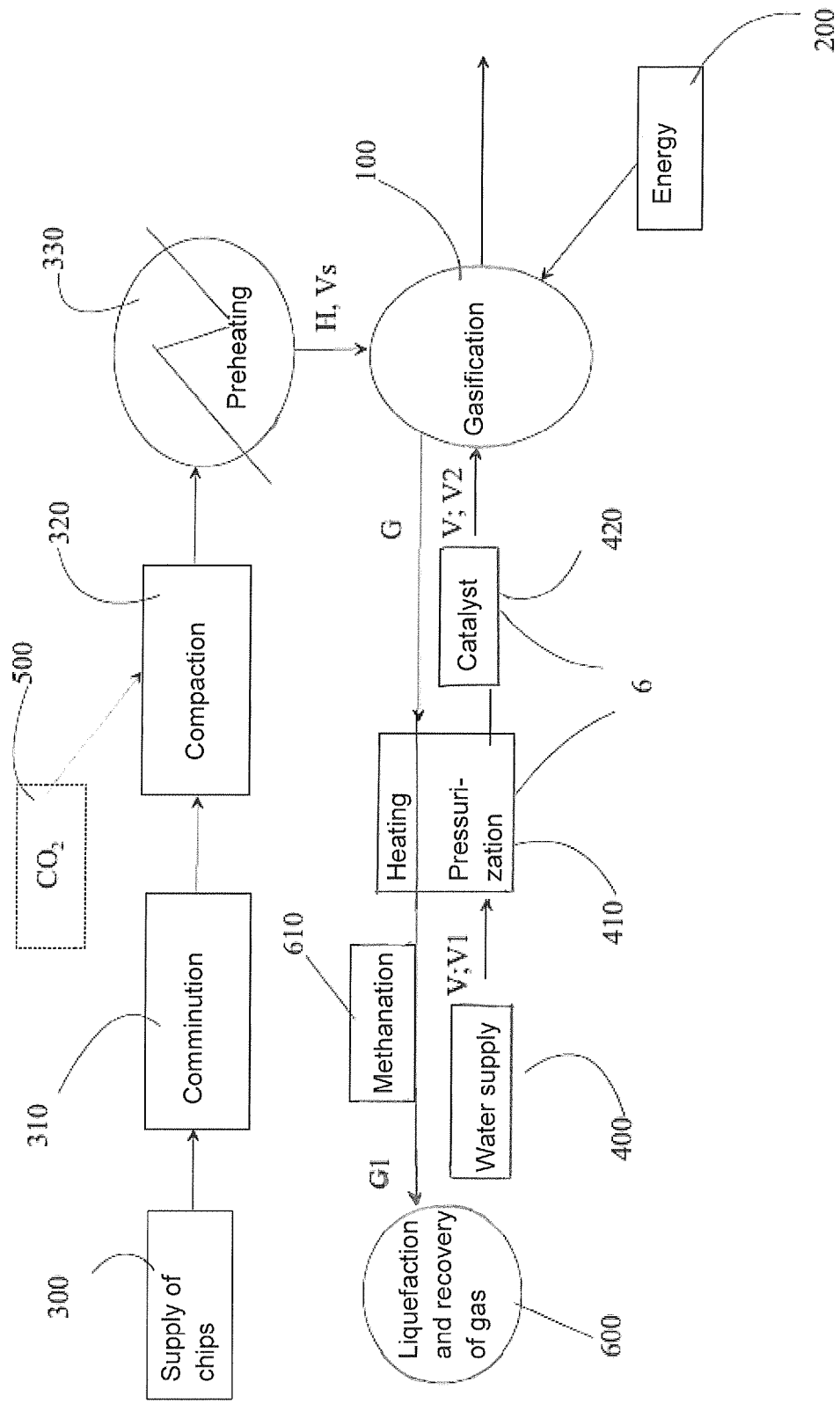
FIG. 1 shows in a schematic presentation the steps of a method according to the invention.
Figure 2:
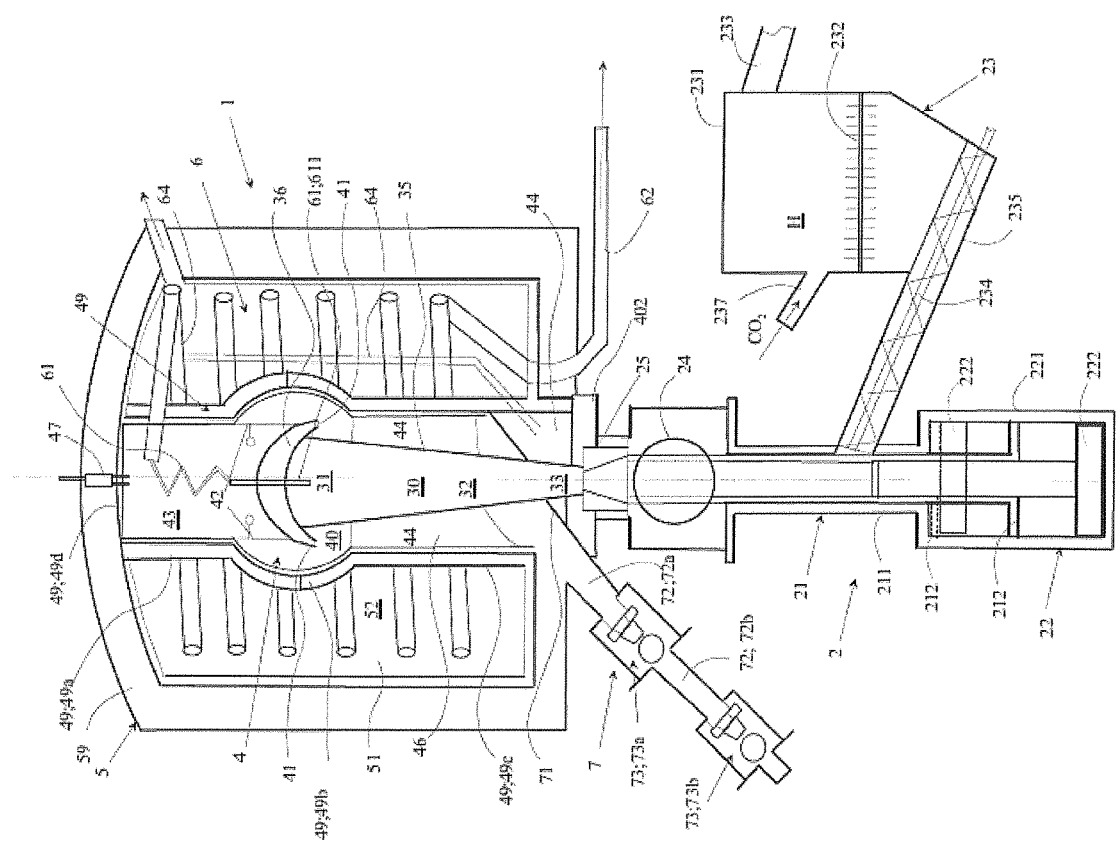
FIG. 2 shows, in a lengthwise sectional view, the chips supply means, a reactor, as well as a reactor chamber for an apparatus used in an arrangement of the invention.

In FIGS. 1 and 2 is shown, in a simplified manner, a method of the invention. The method comprises a supply 300 of chopped wood material, particularly chips, into a reactor 3 of chips feeding means 2, and a subsequently occurring gasification 100 of the chips in a gasification space 31 of the reactor 3. The chips supply 300 includes chopping 310 the chips with a chip container's crusher 232, packing 320 the chips in a densification cylinder 21 through the use of a feeding cylinder 22. Along with the chips may take place an optional carbon dioxide supply 500 for displacing oxygen from chips H. This is followed by the chips H being preheated 330 and delivered by means of the feeding cylinder 22 into the reactor 3. A gasification gas G proceeds into a pipe heat exchanger 6 opening into the upper part of a reaction chamber 4, wherein the gasification gas G has its thermal energy used for heating water to be supplied into the reactor 3 and, at the same time, the gasification gas G is methanated 610 in catalytic Sapatier reaction into a product gas G1. Water V; V2 to be supplied into the reactor's gasification space 31 is first heated by means of a heat exchange with the gasification gas G while being simultaneously conveyed through a catalytic zone 66 for bringing the water V to a supercritical state prior to its introduction into the gasification space 31. After the methanation 610 and a heat transfer 410 (heating of water), the product gas G1 is conveyed to a product gas liquefaction and recovery 600.

Before the product gas G1 is liquefied, there still takes place a removal of water therefrom, as well as a separation of impurities in a scrubber 10.

FIG. 2 shows the upstream end of an apparatus 1 used for the gasification 100 of chips employed in an arrangement of the invention, said upstream end extending from the supply 300 of chips to the supply of gasification gas into the pipe heat exchanger 6.

Figure 3:
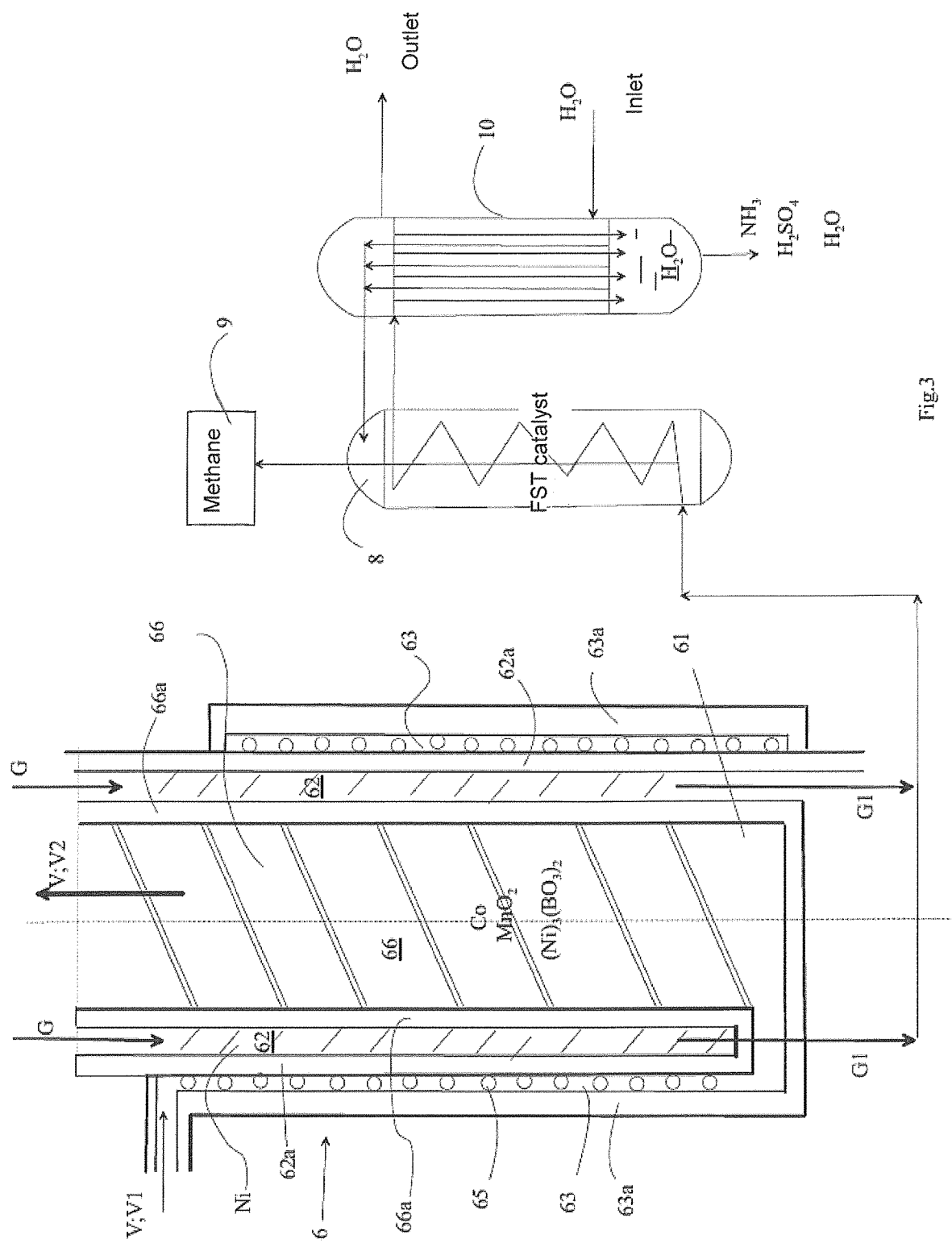
FIG. 3 shows, in a lengthwise sectional view, a heat exchanger and a gas scrubber for an apparatus used in an arrangement of the invention.

On the other hand, FIG. 3 shows parts of the apparatus 1, which are used for the methanation of gasification gas into a product gas G1 and for the simultaneous heating 410 of water V; V1 into supercritical water V; V2, and for the scrubbing 600 of the product gas G1.

The apparatus 1 used in an arrangement of the invention comprises the following principal components: chips supply means 1, a reactor 3, a reaction chamber 4, a cooling liquid tank 5, a catalytic pipe heat exchanger 6, an ash removal device 7, a gas scrubber, a methane separator.

The wood shavings H are delivered 3 with the supply means 2 into the reactor 3. These chips supply means 2 include a chips feeder 23, which is visible in FIG. 2 and which is intended for bringing the crushed chips first into a chips densification cylinder 21. In the densification cylinder 21, the chips are compressed for removing excess water and air. In connection with the densification cylinder 21 is a feeding cylinder 22 by means of which the compressed and crushed chips are intended to be delivered into an interior 30 of the reactor 3 by way of a shut-off valve 24 and a compaction plate 25. The reactor 3 is surrounded by a reaction chamber 4, into which the gasification gas G and the ash discharge from the reactor 3 as subsequently described. The reaction chamber 4 is surrounded by a cooling liquid tank 5 and the gasification gas G is recovered and methanated in a catalytic heat exchanger 6 which is located in conjunction with the reaction chamber 4, commencing from its upper part, extending by way of the reaction chamber 4 and the cooling liquid tank surrounding the same, the catalytic heat exchanger 6 being also provided with means for bringing the water to be supplied into the reactor to a supercritical state by means of a heat exchange with a hot product gas traveling in the heat exchanger 6.

The reaction chamber has its bottom part provided with an ash removal device 7, comprising a base plate, an ash removal conduit, and a two-piece valve assembly 73 present in the ash removal conduit for regulating the removal of ash.

The methanated product gas discharging from the catalytic heat exchanger is cleaned by liquefaction in a gas purifier 8, which operates on the Fischer Tropsch method. In functional communication with the purifier 8 is a water scrubbing unit or scrubber 10 for impurities as well as a methane separator 9, The components of the apparatus 1, which were described above in a sort of general way, shall now be described in more detail. The chips supply means 2 have the chips feeder thereof provided with a storage conveyor 233, such as a screw or chain conveyor, which extends from chips storages (not shown in the figures) to the chips container 231 fitted with a crusher 232. The chips container's 231 crusher 232 is intended for crushing the wood shavings for crushed wood as "pulpy" as possible and consistent in quality, preferably without leaving any splinters, bark slivers or the like. The chips container 231 must be tight as it has connected thereto an optional carbon dioxide supply 237. The purpose of carbon dioxide is to displace air from the crushed chips H so as not to generate too much carbon monoxide in subsequent gasification of the chips H. If necessary, the chips can be heated in the chips container 231 with appropriate heating elements coupled to the chips container. A bottom portion of the chips container is provided with a feed conveyor 234 such as a screw conveyor 234. The feed conveyor 235 has its bottom end located in connection with the chips container 231 while its top end extends to a vertical densification cylinder 21. Between a longitudinal direction of the feed conveyor and a longitudinal direction of the densification cylinder 21 must exist an angle of at least 45 degrees.

From the crusher 232, the crushed chips H fall onto the feeding conveyor 235 by means of which the chips are transferred into the densification cylinder 21 which is in functional communication with the feeding cylinder 22 present therebelow. The densification cylinder 21 comprises an upper cylinder 211 and a tubular compaction piston 212 intended for compressing the chips to a condition as dense as possible for the removal of excess oxygen and air. The feeding cylinder 22 comprises a lower cylinder 221 and a feeding piston 222. The feeding cylinder 22 is intended for delivering the chips into a reactor and for further packing the chips in the densification cylinder 21 by pressing the chips at a top end of the densification cylinder 21 into the reactor 3 through a shut-off valve 24, especially a ball valve, and a compaction plate 25 located downstream thereof in the feeding direction.

The densification cylinder 21 has a filling capacity of about 3.5 liters, into which densification cylinder 21 is squashed about 5-6 liters of crushed chips by the feed conveyor 235. The piston of the feeding cylinder 22 is a hydraulic cylinder piston rod, for example 100 mm in diameter and for example 400 mm+230 mm in stroke length.

The densification cylinder 21 is provided with a tubular compaction cylinder/piston 212 with a tubular piston rod which has a material thickness of about 2 mm and is made of a highly durable material. The tubular compaction piston 212 is machined for a tight tolerance with the feeding piston 222. In the feeding cylinder 22, the lower cylinder 221 has such a tolerance that gaseous substances, such as "excess" water and possible air contained in the chips, will be able to depart from the system upon pre-pressing the chips against said shut-off valve, especially the ball valve 24, with a force of about 20-30 tn.

The shut-off valve 24 is preferably a ball valve 24, which is designed for a pressure of about 350 bar. The compaction plate 25 is a conically tapering throttle plate which opens into a bottom part of the reactors 3 feed pipe 35. The compaction plate 25 packs the chips H to a "final" density, as well as prevents the chips from "trickling" back towards the feeding cylinder 22.

The reactor 3 becomes closed by a feed pipe 35 capable of being provided from the bottom end, by a gasification dome 36 delimiting it from the top end, and by heating devices 42 for the gasification dome 36. The feed pipe 35 comprises a conically expanding tubular reactor, which has a bottom part 200 mm in diameter and which is delimited at the top end by the gasification dome 36. It is the feed pipe 35 and the gasification dome 36 adjacent thereto which define an interior 30 for the feed pipe or reactor, wherein gasification of the crushed and packed chips H takes place. The gasification dome 36, delimiting the feed pipe 35 at the top end, is preferably a hemispherical conduction parabola capable of being heated electrically with the gasification dome heating devices 42. The gasification dome 36 is preferably insulated from outside for example with an aerogel or alumina wool insulation of about 20 mm in thickness. The conduction parabola 36 must be made of a material capable of withstanding the temperature of at least +1700° C. as it is heated to about 1500° C. with an electric current generated by the heating devices 42.

On the other hand, the reactor 3 has its interior 30 defined by a reactor cooling space 33 located at a bottom part of the feed pipe downstream of the supply means 2 in the chips feeding direction, as well by a reactor preheating space 32 and by a reactor gasification space 31 located in the proximity of the gasification dome 36. The gasification space 31 is capable of being supplied with supercritical water by way of a supercritical water inlet pipe 61 with nozzles at its end opening into said gasification space 31. The supercritical water is produced, as subsequently described, with a heat transfer taking place between gasification gas generated in the gasification space 31 and water in a pipe heat exchanger 6.

The temperature of chips in the chips feeding direction rises in the feed pipe 35 rapidly to about 240° C. over a distance of 10 cm. Thus, the formation of tars begins in the interior 30 of the reactor 3 near the compaction plate 25 opening into a bottom end of the feed pipe 35 (at a distance of about 15-20 cm from the compaction plate in the chips advancing direction). The pressure existing in the interior 30 pushes the tars downward to fill all cell tissues of the chips arriving in the interior. The further down tars are able to penetrate in the feed pipe 35, counterclockwise with respect to the chips feeding direction or chips advancing direction, the colder are the chips present in the reactor's cooling space 33. Thus, the tars coagulate to build a plug which contributes to prohibiting the escape of pressure.

After a halfway point of the feed pipe 35, i.e. after the preheating space 32, the temperature of chips H exceeds+ 700° C. and the water, possibly contained in the chips, has turned into a supercritical state, promoting effectively the decomposition of tars into gases.

The actual gasification reaction R of chips takes place in a gasification space, which is at a top end of the feed pipe 35, near the gasification dome 36, and in which a pile is built up by chips H and ash. The chips H present in the gasification space is heated to the temperature of +1000° C.-+ 1200° C. with a hemispherical conduction parabola of the gasification dome 36. The infrared rays generated by the conduction parabola 36 are focused in the middle of a gasification space in the reactor's interior 39, wherein the gasification reaction of chips takes place and into which the catalytically split supercritical water is also pumped by way of a nozzle in the water inlet pipe 61. Water is present in the form of a supercritical fluid above a certain supercritical point at which it has a pressure of 22.064 Mpa (about 217 bar) and a temperature of 647 K (374° C.).

In the reaction (R), the principal components of a gasifying reaction-generated gasification gas G are $H_2$, CO, $CO_2$, $CH_4$ and possibly some higher hydrocarbons, depending on temperature in the gasification space. However, said reaction is controlled by a high partial pressure of water in the reaction (R) in such a way the chips gasification gas G consists for the most part of hydrogen gas, nor is there present hardly any higher hydrocarbons. The gasification space 31 should have an existing pressure of at least 220 bar and a temperature of 374° C.

Under the gasification dome are gasification dome discharge openings 41, leading to a reaction chamber 4 that surrounds the reactor 3. Hence, the gasification gases of about 145 kg/100 kg of chips, generated in the reaction (R), as well as ash, shall exit by way of the discussed discharge openings 41 into the reactor-surrounding reaction chamber 4, such that the gasification gases G discharge through the ash layer as in a traditional co-current downdraft gasifier, whereby a major portion of the gas impurities shall remain in possibly molten ash, the amount of which is about 0.5-1 kg per 100 kg of chips.

The reaction chamber 4 is built up of two pressure vessel hemispheres coupled to each other by welding, bolts or otherwise to form a pressure vessel. Walls 49; 49b defining a middle section of the reaction chamber's 4 interior are half-heart shaped in the reaction chamber shown in the figure, and walls 49; 49c of the reaction chamber's 4 bottom end have attached thereto the reactor's feed pipe 35, as well as an ash removal conduit 72 and a base plate 71 of the ash removal device 7. In addition, the reaction chamber has its bottom part provided with a water point 45 wherefrom it is conducted to the pipe heat exchanger 6 along a cooling water conduit 64 in which it is converted into supercritical water. The reaction chamber 4 has its top end fitted with a safety valve 47, which releases the gas pressure in case the pressure in the reaction chamber 4 rises too much, e.g. to higher than 230 bar.

The reaction chamber 4 has an ash channel 44, which surrounds the reactor preheating space 32 and cooling space 33 present in a bottom part of the feed pipe 35. The reaction chamber 4 has its bottom part provided with an ash removal device 7, which is in communication with the ash channel 44. The hot ash falls from the gas discharge openings downward into the ash channel and towards the ash removal device 7. The gasification gases G, on the other hand, discharge by way of a discharge opening 41 about 20 mm wide into a spherical gas discharge space 40 of the reaction chamber 4, wherein the flow rate of gases G becomes slower. The reaction chamber 4 has its upper part, i.e. a part of the reaction chamber which is defined by the walls 49; 49a, provided with a gas removal space 43 which is in communication with the gas discharge space 40. Into the gas removal space 43 opens the pipe heat exchanger 6, which in this case is a catalytic pipe heat exchanger with the supercritical water inlet pipe 61 extending therein.

It is an objective that the heat of hot ash migrating downward along the ash channel 44 be transferred as effectively as possible to the chips H moving upward in the reactor's interior 30. This is why the ash channel 44 includes heat transfer flanges 46 at a point of the feed pipe 35 in alignment with the reactor preheating space 32 at a bottom part of the feed pipe 35 (approximately halfway along the feed pipe 35).

The reactor 3 has its internal surface insulated with a high temperature resistant insulation material, for example alumina or aerogel. The insulation layer is required to prevent the temperature as high as +1200° C. of the reactor 3 from penetrating into the reaction chamber's pressure vessel structure. To a bottom part of the reactor 3 is welded a sturdy plate, upon which the entire apparatus has been erected and to which is fastened with bolts a cooling liquid tank 5 insulated with PU insulation and surrounding the reaction chamber 4.

The ash removal device includes a chilled base plate 71, which is inclined quite a lot and bent into a curved shape, the ash cooling rapidly. The ash trickles from the base plate into an ash removal conduit 72. An upper part 72a of the ash removal conduit 72 includes an upper valve assembly 73; 73a and a lower part 72b of the ash removal conduit includes a lower valve assembly 73; 73b. Each of the valve assemblies 73; 73a, 73b is provided with a sleeve valve and a ball valve (shut-off valve). The sleeve valves are manipulated with a 221 bar pressure from side to side.

The catalytic pipe heat exchanger 6 is shown in FIGS. 2 and 3. The pipe heat exchanger 6 consists of three concentric tubes. The outermost tube is a pressurized water pipe 63 in which water V; V1 arrives at a pressure of about 225 bar and at a temperature of about 90° C. from a cooling water pipe 64 which comes from the water point 45 (FIG. 2). The pressurized water pipe 63 must have its walls 63a capable of withstanding a pressure of at least 350 bar. The next inner tube is a gas pipe 62 about 54-55 mm in diameter. The difference between a water pressure existing in the pressurized water pipe 63 and a gas pressure of the gas pipe 62 is about 5 bar.

The gasification gas G discharging from the reaction chamber 4 into the gas pipe 62 has a temperature of about 1000° C. at the reaction chamber end of the gas pipe 62, and moreover, the gas pipe 62 must also be capable of withstanding acids present in the gasification gas G. Around the gas pipe 62 is wound a wire of less than 2 mm for a spring that retains the gas pipe 62 and the pressurized water pipe 63 apart from each other and compels the water to travel a longer distance for an effective transfer of heat from the gasification gas G to the water V; V1 flowing in the pressurized water pipe 63. The water temperature rises about 400° C. in the pressurized water pipe. Inside the gas pipe 62 extends a supercritical water inlet pipe 61, which includes a catalyst zone 66 for the decomposition of water V; V1 passing therethrough into supercritical water V; V2 before the water V; V2 arrives in the reactor's gasification space 31.

The supercritical water V; V2, the pumped amount of which is 45 kg/100 kg of dry chips material, is produced by means of heat and catalysts of the catalyst zone 66. Possible catalysts include, among others, cobalt Co, manganese dioxide ($MnO_2$) or nickel borate.

Along with the supercritical water V; V2 can be pumped into the reactor's gasification space 31 also substances which facilitate the bonding of impurities to ash. Along with the water V; V2 can also be pumped other chemicals into the reaction for providing a desired gas composition.

Between the supercritical water pipe 61 and the pressurized water pipe 63 remains a space of about 5 mm, in which the gasification gas G flows at a speed sufficient for possible particles to keep up with the flow. On a surface 62a of the supercritical water pipe 61 is wound a spiral spring. An external surface 63a of the pressurized water pipe 63, an internal surface 66a of the gas pipe 62, as well as the spiral spring can be coated with a catalyst material, e.g. nickel (Ni), for generating a so-called Sapatier reaction in which the gasification gas is methanated. In Sapatier reaction, methane is formed by carbon dioxide and hydrogen. If necessary, more catalyst material can be introduced into the gas space in a steel wool type form for increasing the catalyst surface area. Therefore, the heat of gasification gas G transfers mostly to the supercritical water V; V2 and the temperature of methanated product gases G1, discharging from the heat exchanger 6, drops by about 400° C. prior to passing the product gases G1 to a gas recovery 600.

In the gas recovery 600, water is removed from the product gases G1 and impurities are water washed from the gases in a gas scrubber 10. In the gas scrubber 10, the gases are cooled to below a dew point temperature for the densification and removal of water. In the gas scrubber 10, the gases are conducted in a conventional manner into water, in which are retained those impurities which have not bonded to ash in the reactor 3 and discharged, such as acids, ammonia, sulfuric acid, hydrogen chloride, alkali metals.

From the gas scrubber 10, the gases are conducted to a gas purifier/liquefier 8, in which the product gas G1 is liquefied for example with a catalytic Fischer-Tropsch process by raising temperature of the gases by +250-+300° C. with the heat of through-flowing gases.

As for its composition, the product gas obtained from the catalytic gas purifier 8 should be as follows: hydrogen ($H_2$) about 50%, carbon monoxide (CO) about 25%, and methane ($CH_4$) about 25%.

The non-liquefiable gases, such as methane, are conveyed by way of a refrigerator and a pressure reducing valve into a pressure container 9 to a maximum pressure of about 200 bar, wherefrom the methane gas is collected either to a gas engine or a fuel cell to produce electricity.

The Fischer-Tropsch synthesis and catalysts such as Fe, Co, Ru can be used for the liquefaction of hydrogen gas $H_2$ e.g. into biodiesel or some other desirable chemical compound (ethanol, methanol, DME, etc.).

Presented above are just a few embodiments of the invention and it is obvious for a person skilled in the art that the invention has many other possible implementations within the inventive concept defined in the claims.

Accordingly, even though it is just the gasification of chips into a gasification gas G1 which has been described above, it is self-evident that other chopped wood materials, such as pellets or the like, can also be used for generating a gasification gas. Also carbonaceous biomass, such as logging wastes or the like, can be used the same way.

The process control can be upgraded in such a way that, when biomass or chopped wood material is introduced from an inlet end of the feed pipe 35 into an interior of the reactor 3, the supplied biomass or chopped wood material is measured or assessed for its water content. The measured or assessed water content of biomass or chopped wood material delivered into the reactor is used as a basis for regulating the amount of free supplementary water/supplementary steam to be introduced into the reactor. The water content of biomass or chopped wood material can be assessed or measured before or after its delivery into the interior of the reactor 3.

LIST OF REFERENCE NUMERALS

1 Apparatus
2 Chips supply means
21 densification cylinder
211 upper cylinder
212 tubular compaction piston
22 feeding cylinder
221 lower cylinder
222 feeding piston
23 Chips feeder
231 chips container
232 crusher
233 storage conveyor
234 screw conveyor
235 feed conveyor
237 carbon dioxide supply
24 shut-off valve, ball valve
25 compaction plate
3 Reactor
30 reactor's interior
31 reactor's gasification space
32 reactor's preheating space
33 reactor's cooling space
35 feed pipe
36 gasification dome
4 Reaction chamber
40 chamber discharging space
41 gasification dome discharge opening, gas inlet opening to the chamber
42 gasification dome heating devices
43 gas removal space
44 ash channel
46 heat transfer flanges
47 safety valve
49 walls of the reaction chamber
49; 49*a* wall of the reaction chamber's upper part
49; 49*b* wall of the reaction chamber's middle part
49; 49*c* wall of the reaction chamber's middle part
49; 49*d* ceiling of the reaction chamber
5 Cooling liquid tank
51 liquid space of the tank
52 cooling water
59 walls of the tank
6 Catalytic pipe heat exchanger
61 supercritical water inlet pipe
62 gas pipe
63 pressurized water pipe
64 cooling water pipe
65 spiral spring
66 catalytic zone
7 Ash removal device
71 base plate
72 ash removal conduit
72*a* upper part of the ash removal conduit
72*b* lower part of the ash removal conduit
73 valve assembly
73*a* upper valve assembly
73*b* lower valve assembly
8 Gas purifier/liquefier
9 Methane separator
10 gas scrubber
100 Gasification of chips
200 Supply of energy
300 Supply of chips
310 comminution of chips
320 compaction of chips
330 preheating of chips
400 Water supply
410 heating of water
500 Carbon dioxide supply
6000 Recovery and conversion of product gas
610 Methanation
H Chips
G Gasification gas
G1 Product gas
V Water flow into reaction chamber
V1 water flow arriving in heat exchanger
V2 flow of supercritical water into gasification space

The invention claimed is:

1. An arrangement for preparing a gas (G) in a closable reactor by supplying said reactor with carbon-based biomass or chopped wood, or plastic or plastic based material, in substantially oxygen-free conditions, by allowing the biomass or wood material, or plastic or plastic based material to gasify at a high temperature, and by recovering the gas (G) generated in a gasification reaction (R), wherein the arrangement comprises:

a reactor surrounded by a reaction chamber; and
a catalytic pipe heat exchanger;
the reactor having an interior space defined by a feed pipe having an inlet end and an outlet end,
the inlet end being configured to receive carbon based biomass or chopped wood or plastic or plastic based material, and being closable with a shut-off valve, the outlet end being adjoined with a heatable gasification dome, and a gasification space of the reactor being formed at the outlet end below the gasification dome; and the catalytic pipe heat exchanger comprising a supercritical water inlet pipe having an inlet into the gasification space, and wherein the catalytic pipe heat exchanger consists of three concentric pipes, the outermost of the pipes being a pressurized water pipe configured to flow cooling water, the middle one of the pipes being a gas pipe configured to flow gasification gas (G) from the reaction chamber to recovery, and the innermost pipe being the supercritical water inlet pipe configured to provide additional free water or water vapor in supercritical state into the reactor.

2. The arrangement according to claim 1, wherein the gas pipe and the supercritical water inlet pipe are located and configured such that the thermal energy of the gas can transfer to the free water/water vapor to be delivered into the reactor's interior.

3. The arrangement according to claim 1, wherein the gasification space is adapted to have an existing pressure of 217 bars and temperature of 374° C.

4. The arrangement according to claim 1, wherein the gasification space is adapted to have a pressure of at least 220 bars and a temperature is of 700-1300° C.

5. The arrangement according to claim 1, wherein the supercritical water inlet pipe is configured to flow an oxygen-binding substance along with the supercritical water.

6. The arrangement according to claim 1, wherein the amount of the free supercritical water flow from the supercritical water inlet pipe into the gasification zone can be regulated, whereby in the gasification reaction (R) most of the carbon present in the biomass arriving in the reactor is converted into carbon monoxide and carbon dioxide.

7. The arrangement according to claim 6, configured to discharge ash having a content of unreacted carbon not higher than 1%.

8. The arrangement according to claim 1, wherein the heat exchanger is a catalytic spiral heat exchanger and is located in a liquid space of a cooling liquid tank surrounding the reaction chamber, said catalytic heat exchanger having inside itself a catalytic zone for converting carbon dioxide and hydrogen present in the gas (G) into alkanes.

9. The arrangement according to claim 8, wherein the heat exchanger is a catalytic pipe heat exchanger, wherein water is heated to a supercritical state mostly with thermal energy of the gas (G) produced in the gasification reaction (R).

10. The arrangement according to claim 9, wherein a spiral spring coated with a catalyst material is coiled around the supercritical water pipe, and the external surface of the pressurized water pipe and the internal surface of the gas pipe are coated with the catalyst material, thereby converting the carbon dioxide gas and hydrogen gas present in the gasification gas (G) generated in the reaction (R) into methane and water in a so-called Sabatier reaction (1):

$$CO_2 + 4H_2 \leftrightarrow CH_4 + 2H_2O \qquad (1).$$

11. The arrangement according to claim 6, wherein the arrangement is configured to regulate the amount of supercritical water supplied from the supercritical water pipe such that aggregate amount of water being the water delivered into the interior of the reactor along with wood material and the free supercritical water to be delivered into the gasification space is such that the thermal energy contained therein is sufficient to increase in the heat exchanger the temperature of water to introduced into the reaction from about 300° C., to at least about 700° C.

12. The arrangement according to claim 6, configured to regulate the amount of the free supercritical water flow from the supercritical water inlet pipe into the gasification zone to be at least 15 kg per 100 kilograms of dry wood material to be delivered into the reactor's interior.

13. The arrangement according to claim 1, wherein the supercritical water inlet pipe has a nozzle extending into the gasification space.

14. The arrangement according to claim 1, wherein the arrangement comprises a hydraulic cylinder against the shut-off valve for removal of substantially all air and excess water from the biomass or material prior to its delivery into the interior of the reactor.

15. The arrangement according to claim 1, wherein the reaction chamber has a discharge space adapted to receive the gas (G) departed from the gasification space through a gasification dome discharge opening located between the gasification dome and the feed pipe, such that the gas (G) passes through a layer of ash.

16. The arrangement according to claim 1, wherein a lower part of the reactor is a preheating space, which is adapted to be heated by hot ash migrating gravitationally downward in the reaction chamber, and the preheating space has a temperature higher than 700° C. for converting tars present in wood material into gasification gases.

17. The arrangement according to claim 16, wherein the reactor's interior has a pressure such that water (Vs) arriving in the interior along with wood material, becomes supercritical in the preheating space.

18. The arrangement according to claim 1, wherein the reaction chamber has at its bottom end an ash removal device, which is provided with valve assemblies for removing ash from the discharge space.

19. The arrangement according to claim 1, wherein in a lower part of the feed pipe in the proximity of a shut-off valve a cooling is provided and the lower part of the feeding pipe is a reactor cooling space in which the temperature is less than 100° C., for the cooling and solidification of tars produced in the heating of the chips (H).

20. The arrangement according to claim 5, wherein the oxygen-binding substance is carbon or sodium.

21. The arrangement according to claim 7, wherein the content of unreacted carbon is not higher than 0.5%.

22. The arrangement of claim 8, wherein the catalytic zone comprises preferably nickel or alumina.

23. The arrangement of claim 9, wherein the catalytic pipe heat exchanger is a countercurrent pipe heat exchanger.

24. The arrangement according to claim 12, configured to regulate the amount of the free supercritical water flow from the supercritical water inlet pipe into the gasification zone to be 45-55 kg per 100 kilograms of dry wood material to be delivered into the reactor's interior.

* * * * *